United States Patent [19]

Wong et al.

[11] 4,304,773

[45] Dec. 8, 1981

[54] NOVEL BENDROFLUMETHIAZIDE FORMULATIONS AND METHOD

[75] Inventors: Thomas M. Wong, North Brunswick; Mahendra R. Patel, East Brunswick, both of N.J.

[73] Assignee: E. R. Squibb & Sons, Inc., Princeton, N.J.

[21] Appl. No.: 163,128

[22] Filed: Jun. 26, 1980

[51] Int. Cl.$^3$ .................... A61K 31/54; A61K 47/00
[52] U.S. Cl. .................................. 424/246; 424/362
[58] Field of Search ........................ 424/246; 424/362

[56] References Cited

U.S. PATENT DOCUMENTS 3,265,573  8/1966  Goldberg ........................... 424/246

OTHER PUBLICATIONS

Merck Index, 9th Ed., 1976, entry no. 1042.
Lachman et al., "The Theory & Practice of Industrial Pharmacy", 2nd Ed. (1976), pp. 325–333.

*Primary Examiner*—Frank Cacciapaglia, Jr.
*Attorney, Agent, or Firm*—Lawrence S. Levinson; Burton Rodney

[57] ABSTRACT

New bendroflumethiazide formulations in solid form are provided which are characterized by excellent disintegration and dissolution capabilities even after long periods of storage. The new bendroflumethiazide formulations, for example, in the form of tablets, contain in addition to bendroflumethiazide, a combination of microcrystalline cellulose which serves as a diluent and aids in disintegration of the tablets, lactose which serves as a diluent, optionally starch (in the gelatinized form) which serves as a disintegrant, and one or more auxilliary disintegrants, such as sodium carboxymethyl starch, a tablet lubricant, such as magnesium stearate, and a colorant, if desired.

A method for preparing the above formulations is also provided.

10 Claims, No Drawings

NOVEL BENDROFLUMETHIAZIDE FORMULATIONS AND METHOD

FIELD OF THE INVENTION

The present invention relates to bendroflumethiazide formulations, in solid form, especially tablets, which have improved disintegration properties and dissolution properties even after storage for long periods of time, and to a method for preparing such formulations.

BACKGROUND OF THE INVENTION

Bendroflumethiazide (the generic name for 3-benzyl-3,4-dihydro-7-sulfamoyl-6-trifluoromethyl-1,2,4-benzothiadiazine 1,1-dioxide) is known as a diuretic and antihypertensive agent as disclosed in U.S. Pat. No. 3,265,573. When formulated as a tablet, bendroflumethiazide is usually in admixture with gum acacia which serves as a binder, corn starch which serves as a disintegrant, together with a lactose diluent, lubricant and water-soluble dyes.

The prior art bendroflumethiazide tablets are prepared by first dissolving part of the gum acacia binder and water-soluble dyes in water, adding lactose to the resulting solution, drying the mixture, reducing the resulting particles to fine granules, and then mixing such granules with the bendroflumethiazide, cornstarch and remainder of the gum acacia, and compressing the mixture into tablets. Such tablet formulations disintegrate in water after about 9 minutes and have good dissolution properties upon aging. However, tablet formulations which have improved disintegration properties and dissolution properties and are faster and cheaper to manufacture would still be most desirable.

DESCRIPTION OF THE INVENTION

In accordance with the present invention, a unique bendroflumethiazide formulation in solid form, especially in tablet form, is provided wherein gum acacia is not employed and therefore water is not mixed with any of the formulation ingredients. Accordingly, the bendroflumethiazide formulation of the invention is faster and less expensive to manufacture than prior art formulations, and is more stable and has faster disintegration and dissolution times than prior art formulations. In addition, since water is not employed in the formulation of the invention, the risk of drug degradation due to water is eliminated.

The bendroflumethiazide formulation of the invention contains from about 1 to about 20% and preferably from about 2.5 to about 10% bendroflumethiazide, from about 10 to about 60% and preferably from about 15 to about 40% of microcrystalline cellulose which functions as a diluent and disintegrant, from 0 to about 50% and preferably from about 15 to about 30% by weight of starch which functions as a disintegrant, from about 0 to about 5% and preferably from about 2 to about 3% by weight of an auxiliary disintegrant, such as sodium carboxymethyl starch, from about 10 to about 80% and preferably from about 30 to about 70% of a diluent, such as lactose, from about 0 to about 4% and preferably from about 0.5 to about 2% by weight of a colorant, if desired. All of the above percentages are based on the weight of the total composition especially when formulated as a tablet.

The microcrystalline cellulose will preferably have an average particle size of from about 50 to about 100 microns so that it does not impair flow properties. Preferred is the Avicel brand microcrystalline cellulose manufactured by FMC Corp.

The optional starch component of the formulation of the invention will preferably be of the gelatinized type to impart better flow properties and compressibility. Preferred is StaR$_x$ brand starch manufactured by Colorcon, Inc.

The auxiliary disintegrant is preferably sodium carboxymethyl starch of the Explotab brand manufactured by Edward Mendall Company, Inc., although modified cellulose (Ac-Di-Sol) or cross-linked polyvinyl pyrrolidone may also be used.

As indicated, the formulation of the invention will contain one or more conventional tabletting diluents such as lactose and/or starch with lactose being preferred.

The tabletting lubricant present in the formulation of the invention may comprise conventional type tabletting lubricants, such as magnesium stearate, cornstarch, talc, stearic acid or mixtures thereof with magnesium stearate being preferred.

In addition to the above ingredients, the formulation of the invention may also optionally include conventional tabletting ingredients, such as acacia, polyvinyl pyrrolidone, and the like.

In carrying out the present invention, the microcrystalline cellulose will be employed in a weight ratio to the bendroflumethiazide of within the range of from about 5:1 to about 24:1, and preferably from about 6:1 to about 11:1, the starch will be employed in a weight ratio to the bendroflumethiazide of from about 0:1 to about 20:1, and preferably from about 5:1 to about 9:1, and the auxiliary disintegrant will be employed in a weight ratio to the bendroflumethiazide of within the range of from about 0:1 to about 2:1, and preferably from about 0.5:1 to about 1:1.

Preferred tablet formulations in accordance with the present invention are set out below.

| Ingredient | Most Preferred % By Weight |
| --- | --- |
| Bendroflumethiazide | 2.5 to 10 |
| Microcrystalline cellulose | 24 to 28 |
| Starch (gelatinized) | 21 to 24 |
| Sodium carboxymethyl starch | 2 to 3 |
| Lubricant | 0.1 to 0.5 |
| Diluent | 40 to 50 |
| Color | 0 to 1.5 |

Further in accordance with the invention, the tablet formulation of the invention is prepared by simply mixing the bendroflumethiazide, microcrystalline cellulose, optionally starch in gelatinized form, and sodium carboxymethyl starch and optionally color, screening the resulting blend, adding lubricant, such as magnesium stearate, diluent, such as lactose, and then compressing the mixture into tablets. Water and gum acacia are not necessary and are not employed.

The solid bendroflumethiazide formulation of the invention may comprise a tablet, capsule, pill, powder and preferably, a tablet which may take any conventional shape or size, such as square, round, oblong, pill-shape and the like. These solid forms may be formulated in dosages of 1–20 mg amounts.

Even in the case of the high dosage forms, the solid formulations of the invention will quickly disintegrate in water after only 1 minute and will dissolve in 0.1 N HCl within 15 minutes.

The following Examples represent preferred embodiments of the present invention.

EXAMPLE 1

A bendroflumethiazide tablet having the following composition is prepared as described below.

| Composition | Amount Parts by Weight |
|---|---|
| Bendroflumethiazide, NF to provide ca | 2.5 |
| Microcrystalline cellulose (Avicel PH 101, NF) ca | 28 |
| Gelatinized starch (StaRx-1500 Starch, USP) | 21 |
| Sodium carboxymethyl starch (Explotab) | 2 |
| F.D.C. Green Lake Blend | 1 |
| Lactose, Fast Flo (Foremost) | 45 |
| Magnesium Stearate, USP | 0.30 |

The microcrystalline cellulose is mixed with the bendroflumethiazide, color, sodium carboxymethyl starch, and gelatinized starch and the resulting blend is passed through a Fitzmill using screen size #2 and medium speed. The lactose and magnesium stearate are then added and the mixture is mixed well. Thereafter, the so-formed blend is compressed into tablets.

The bendroflumethiazide tablets formed as described above are formed to quickly disintegrate and dissolve in water even upon storage.

EXAMPLE 2

A bendroflumethiazide tablet having the following composition is prepared as described below.

| Composition | Amount Parts by Weight |
|---|---|
| Bendroflumethiazide, NF to provide ca | 5 |
| Microcrystalline cellulose (Avicel PH 101, NF) ca | 40 |
| Gelatinized starch (StaRx-1500 Starch, USP) | 33 |
| Sodium carboxymethyl starch (Explotab) | 3 |
| F.D.C. Green Lake Blend | 1 |
| Lactose, Fast Flo (Foremost) | 67 |
| Magnesium Stearate, USP | 6.5 |

The microcrystalline cellulose is mixed with the bendroflumethiazide, sodium carboxymethyl starch, color, and starch and the resulting blend is passed through a Fitzmill using screen size #2 and medium speed. The lactose and magnesium stearate are then added and the mixture is mixed well. Thereafter, the so-formed blend is compressed into tablets.

The bendroflumethiazide tablets formed as described above are found to quickly disintegrate and dissolve in water even upon storage.

EXAMPLE 3

A bendroflumethiazide tablet having the following composition is prepared as described below.

| Composition | Amount Parts by Weight |
|---|---|
| Bendroflumethiazide, NF to provide ca | 10 |
| Microcrystalline cellulose (Avicel PH 101, NF) ca | 60 |
| Gelatinized starch (StaRx-1500 Starch, USP) | 58 |
| Sodium carboxymethyl starch (Explotab) | 5 |
| F.D.C. Green Lake Blend | 3 |
| Lactose, Fast Flo (Foremost) | 113 |
| Magnesium Stearate, USP | 0.8 |

The microcrystalline cellulose is mixed with the bendroflumethiazide, color, sodium carboxymethyl starch, and gelatinized starch and the resulting blend is passed through a Fitzmill using screen size #2 and medium speed. The lactose and magnesium stearate are then added and the mixture is mixed well. Thereafter, the so-formed blend is compressed into tablets.

The bendroflumethiazide tablets formed as described above are found to quickly disintegrate and dissolve in water even upon storage.

What is claimed is:

1. A solid bendroflumethiazide formulation, substantially free of water, having excellent disintegration and dissolution properties even upon aging, consisting essentially of bendroflumethiazide, microcrystalline cellulose, and starch as a disintegrant in an amount within the range of from about 15 to about 30% by weight of the formulation and auxiliary disintegrant selected from the group consisting of sodium carboxymethyl starch, modified cellulose gum or polyvinyl pyrrolidone, the microcrystalline cellulose being present in a weight ratio to the bendroflumethiazide of within the range of from about 5:1 to about 24:1, the starch being present in a weight ratio to the bendroflumethiazide of within the range of from about 5:1 to about 9:1 and the auxiliary disintegrant being present in a weight ratio to the bendroflumethiazide of within the range of from about 0:1 to about 2:1.

2. The formulation as defined in claim 1 further including from about 10 to about 80% by weight of a lactose diluent or starch diluent and from about 0.1 to about 0.5% by weight of a lubricant selected from the group consisting of magnesium stearate, cornstarch, talc, stearic acid and mixtures thereof.

3. The formulation as defined in claim 1 wherein the microcrystalline cellulose is present in an amount of from about 10 to about 60% by weight, and the auxiliary disintegrant is present in an amount of from about 0 to about 5% by weight.

4. The formulation as defined in claim 1 wherein the microcrystalline cellulose is present in a weight ratio to the bendroflumethiazide of within the range of from about 6:1 to about 11:1, and the auxiliary disintegrant is present in a weight ratio to the bendroflumethiazide of within the range of from about 0.5:1 to about 1:1.

5. The formulation as defined in claim 1 wherein the starch is gelatinized corn starch.

6. The formulation as defined in claim 1 wherein the auxiliary disintegrant is sodium carboxymethyl starch or modified cellulose gum.

7. The formulation as defined in claim 1 wherein the auxiliary disintegrant is sodium carboxymethyl starch.

8. The formulation as defined in claim 1 comprising microcrystalline cellulose, gelatinized starch, and sodium carboxymethyl starch.

9. The formulation as defined in claim 2 wherein the diluent is lactose.

10. The formulation as defined in claim 2 wherein the lubricant is magnesium stearate.

* * * * *